United States Patent [19]

Lee et al.

[11] Patent Number: 4,753,657
[45] Date of Patent: Jun. 28, 1988

[54] FIXATION OF IMPLANTS IN BONE

[75] Inventors: Alan J. C. Lee; Robin S. M. Ling, both of Exeter, England

[73] Assignee: University of Exeter, Devon, England

[21] Appl. No.: 691,627

[22] Filed: Jan. 15, 1985

[30] Foreign Application Priority Data

Jan. 16, 1984 [GB] United Kingdom ............... 8401059

[51] Int. Cl.$^4$ ................................................ A61F 2/28
[52] U.S. Cl. .......................................... 623/16; 623/23
[58] Field of Search ............... 3/1, 1.9, 1.51, 1.911, 3/1.912, 1.913; 128/92 C, 92 CA

[56] References Cited

U.S. PATENT DOCUMENTS

| 3,793,650 | 2/1974 | Ling et al. | 3/1.913 |
| 4,064,567 | 12/1977 | Burstein | 623/16 |
| 4,158,893 | 6/1979 | Swanson | 3/1.91 |
| 4,314,381 | 2/1982 | Koeneman | 3/1.91 |
| 4,406,023 | 9/1983 | Harris | 623/22 |

FOREIGN PATENT DOCUMENTS

| 85147 | 11/1902 | European Pat. Off. . |
| 0041591 | 12/1981 | European Pat. Off. ............ 3/1.912 |
| 86879 | 11/1982 | European Pat. Off. . |
| 115564 | 8/1983 | European Pat. Off. . |
| 8302555 | 8/1983 | World Int. Prop. O. . |
| 1556814 | 11/1979 | United Kingdom . |

Primary Examiner—Richard J. Apley
Assistant Examiner—David J. Isabella
Attorney, Agent, or Firm—Larson and Taylor

[57] ABSTRACT

A bone implant assembly having an implant element whereof a stem portion is for insertion into a bone cavity, and wedge means for wedging between a proximal region of the cavity wall and the stem. The stem is tapered so that deeper insertion urges the wedge means against the wall. The wedge means may comprise lateral and medial wedges. Each may comprise a stem engaging portion with a low-friction surface, and an outer, wall engaging portion having a surface adapted for non-slip engagement, being a high friction surface and/or adapted for ingrowth of bone.

10 Claims, 2 Drawing Sheets

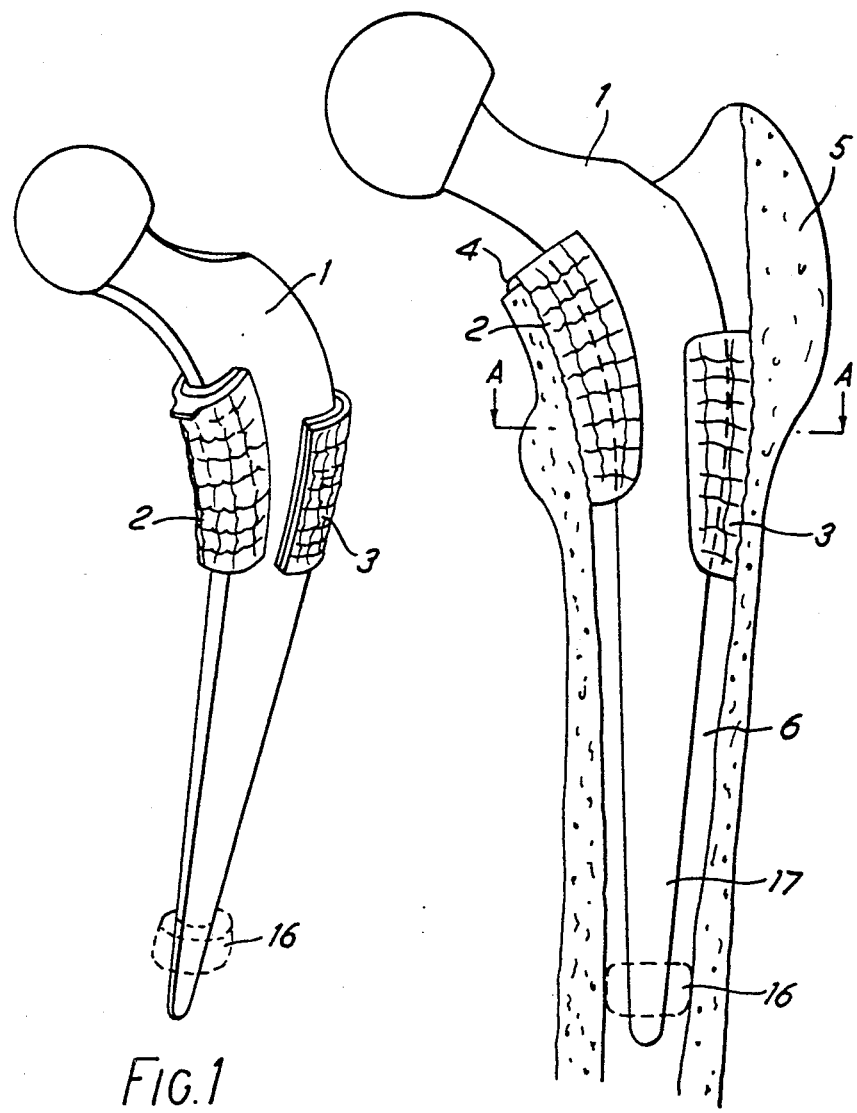

FIXATION OF IMPLANTS IN BONE

BACKGROUND OF THE INVENTION

This invention relates to the fixation of implants in bone. It particularly relates to fixation of the femoral component of a total replacement hip joint.

As total hip replacement becomes a procedure that is used in patients who are younger when the operation is performed, so it becomes necessary to have a method of fixation for the components of the implant in bone which is reliable and safe over very extended periods, e.g. for 20, 25 or 30 years or more. Conventional total replacement hip joint femoral stems are most often fixed in position inside the femur with polymethylmethacrylate bone cement. It has been suggested by a number of investigators that the use of bone cement may not give adequate fixation for the very long periods now being contemplated, and that a fixation system which does not use bone cement would be preferable. A number of such cementless fixation systems have been developed by various inventors throughout the world using either a "press fit" system or an "ingrowth" system. The press fit system relies on the surgeon producing an accurately shaped cavity in the femur into which the stem of the femoral implant will fit exactly. Loads are then transmitted from the implant stem directly to the bone. The ingrowth system relies upon a somewhat less accurate fit, but still a close fit, of the implant in the bony cavity. Bone is then expected to grow up to the implant surface, which is usually rough or structured, and lock the implant in place; or in a variation of this system, bone grows up to the implant surface and penetrates into the surface which is made porous to allow this penetration or ingrowth to take place. There are a number of difficulties with both the press fit and the ingrowth systems. Both need a large number of variations of size of femoral component to cope with the large variation of size of femur found in the group of patients to be treated. If a sufficient range of implants is not available then proper support of the implant by good quality, strong bone cannot be achieved in every case. If bone is to grow into, or onto, the surface of the implant, then the relative movement between the implant and the bone must be very small. In particular, shearing movement must be avoided. This means that a patient with a conventional "cementless" stem must be prevented from weight bearing for extended periods which is commonly not possible, and is usually contra-indicated in elderly patients. Because the shape of the cavity which has to be produced in the bone of the femur is essentially an irregular non-uniform but generally rectangular cross-section at the proximal (i.e. upper) end and essentially a circular, reasonably uniform cross-section at the distal (i.e. lower) end it is easy to obtain close fitting of the implant at the distal, circular end, but considerably more difficult at the proximal, irregular shaped end. However, it is necessary to transmit load at the proximal rather than the distal end to ensure disuse osteoporosis, or disuse atrophy, does not take place. Since load transmission with conventional cementless devices relies on the closeness of the fit of the implant in the bone, it is common to obtain better load transmission at the wrong end of the implant with potentially serious consequences to the patient. If bone is encouraged to grow up to and into the whole surface of an implant, the total surface area of metal in direct contact with the bone is very large. Consequently, the surface area available for corrosion, or which can take part in ionic transfer processes, is very large and the possibility of sensitisation of the patient to the materials of the implant is increased. Finally, the fatigue strength of the implant may be reduced by the effect of the rough or porous or sintered surface which is given to the implant.

SUMMARY OF THE INVENTION

According to the present invention there is provided a bone implant assembly comprising a bone implant element having a stem portion for insertion into a bone cavity, and wedge means adapted to engage with respective surfaces both the wall of the cavity and the stem portion, generally at the proximal end region thereof, so as to permit relative displacement of the stem portion. The stem will generally be tapered, so that its displacement can urge the wedge means against the cavity wall, preferably leading to static, compressive contact.

Preferably the wedge means has a portion of low-friction, low-wear material which provides the stem engaging surface.

Preferably the wall engaging surface of the wedge means is provided by a biocompatible material such as an implant grade metal. The wall engaging surface is preferably adapted for non-slipping contact with the wall, e.g. by frictional engagement and/or by being subject to ingrowth by the bone. It should encourage the growth of bone or tissue right up to the wedge means.

For hip joint replacement, the implant assembly may have as the implant element a generally conventional collarless total hip component similar in shape to that developed by the present inventors and shown in U.K. Patent Specification No. 1409054. The wedge means may comprise two wedge like devices, for engaging the lateral and medial sides of the stem respectively. They may extend partially around the anterior and posterior sides of the stem. Alternatively there may be separate anterior and posterior wedges. The wedges may be mutually connected, or in contact, or wholly separate. Each wedge may comprise a component of a low friction material, such as high density polyethylene, which provides the stem engaging surface; and an outer portion of implant grade metal of the same composition as the stem, which provides or bears the wall-engaging surface. The outer (wall-engaging) surface may be made as a rough surface, or as a porous surface or may have a sintered porous surface which is to be in contact with the bone. As an alternative, the smooth or structured outer surface of the metal may have a coating of a biocompatible ceramic material, such as alumina, applied over it by spray coating or some other method, so that in use the bone is in contact with the ceramic material. In use, the stem portion is able to slide on the inner polymer surface causing the two wedges to move outwards against the bone. The wedges are brought into close, static, contact with the bone and are able to transmit load from the implant to the bone. The wedges are placed in the proximal area of the stem, thus ensuring load transmission takes place at the proximal and not the distal end of the implant. The use of the wedges, which may be provided with a range of interchangeable polymer inserts differing in thickness or shape, means that the fitting of the implant to the cavity (usually the femoral canal) can be achieved with a small range of standard stems, and gives individually tailored stem systems. The relative movement caused by load applications to the implant is taken up at the implant/polymer interface and not at the implant wedge/bone interface thus promoting good fixation. This lack of movement at the implant/bone interface should mean that weight bearing can be resumed by the patient very quickly after his operation. The amount of metal surface in direct contact with the bone is smaller than with conventional cementless implants and can be almost entirely eliminated by the ceramic coating technique. The fatigue strength of the stem is not reduced and will remain the same as with a conventional cemented stem.

In further aspects the invention provides wedge means for use with a bone implant element, and a kit of parts comprising wedge means of adjustable thickness (e.g. comprising a metal outer portion and a plurality of different low friction components), optionally together with one or more implant elements which may have different stem portions. Of course, the invention in its various aspects is mainly concerned with implant fixation without the use of cement.

BRIEF DESCRIPTION OF THE DRAWINGS

FIG. 1 is a view of the femoral component of a total replacement hip joint with medial and lateral wedges embodying the invention in position and an optional tip spacer shown dotted;

FIG. 2 is a diagram showing the femoral implant located in the medullary canal of a femur;

DESCRIPTION OF THE PREFERRED EMBODIMENTS

Figure 3:
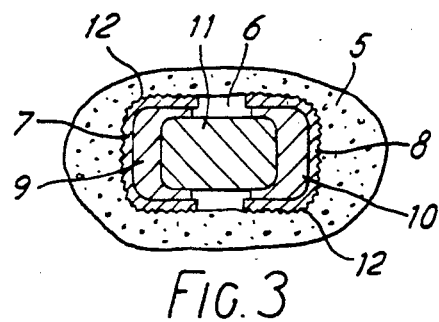
FIG. 3 is a cross-section through the femur and implant as defined by Section A—A of FIG. 2.

Referring first to the embodiment shown: FIGS. 1 to 3, a medial wedge 2 and lateral wedge 3 are mounted on a collarless femoral stem 1 so that the stem is able to slide within the two wedges in a generally vertical direction, i.e. up and down the centre line of the stem. Since the stem is tapered in this direction, such movement will cause the wedges to be displaced outwards as the stem moves downwards.

Figure 4:
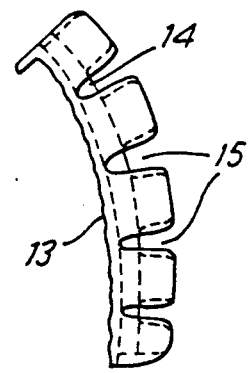
FIG. 4 shows a second embodiment of the wedge components.

In use the medial wedge 2 and lateral wedge 3 are placed on the femoral component 1 and the femoral component and wedges are pushed down into the previously prepared medullary canal 6 of the femur 5. A lip 4 may be fitted onto or integral with the top of the medial component 2 so that it rests on the cut surface of the neck of the femur and prevents any possibility of the medial wedge moving distally down the medullary canal. Some detail of the construction of the wedges is seen in FIG. 3. The wedges fit around the femoral component 11. They have inner lining portions 9,10 suitably of polymeric material, e.g. implantable quality high density polyethylene, or other low friction and low wear biocompatible polymer. The lining portions are in contact with the stem and may slide up and down relative to the stem. A respective outer shell of metal 7,8 embraces each polymer portion 9, and the shell and the polymer are fixed together. The sizes of the polymer portions 9, 10 can be varied to make proper fitting of the components in medullary canals of different sizes possible. The outer surface 12 of a metal shell may be of a structured texture, either a rough surface, or a porous surface or a sintered surface so that bone can grow into intimate contact with the surface. As an alternative the surface 12 of the shells may be coated with a biocompatible ceramic, such as alumina, which will also allow bone to grow into intimate contact with it. An alternative shape for the shells and polymer lining portions is shown in FIG. 4, which shows the medial shell; the lateral shell can be of a similar form. In this version a series of slots 15 is cut through the metal 13 and the polymer lining 14 such that the shell is able to deform more easily in one sense, to conform to the shape of the femoral component and the medullary canal. The outer surface of the shell may have the same alternative structures as described previously.

The action of the stem taper on the wedges forcing the medial and lateral wedges into close contact with the bone is favourable for bone formation onto the wedges because the contact is not moving and is generally compressive. By varying the degree and nature of the surface 12 of the wedges and by varying the length of the wedges it should be possible to induce bone formation in selected regions, e.g. in only the upper end of the femur in primary procedures, or more extensively in revision procedures.

Figure 7:
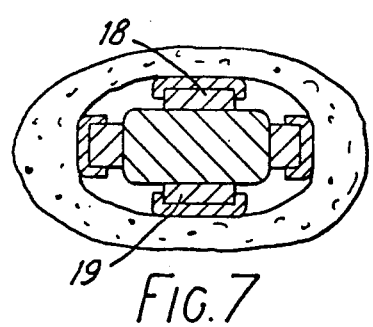
FIG. 7 is a cross-section of the femur showing a third embodiment of a fixation device.
Figure 8:
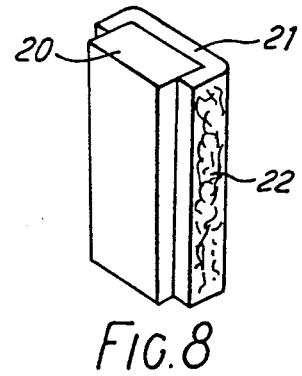
FIG. 8 is a sketch of one component of the fixation device shown in FIG. 7.

The medial and lateral wedges described previously are shaped so that they both extend onto the anterior and posterior sides of the stem 1. In an alternative form shown in FIGS. 7 and 8 the medial and lateral wedges rest only on the medial and lateral surfaces, and two further wedges, the anterior wedge 18 and posterior wedge 19 are used as well to ensure positive location. In this alternative form each wedge has a polymer lining portion 20 inside a metal shell 21, generally as previously described in principle. The outer surface of the metal shell 22 is structured or coated as previously described. This form of fixation may be preferred when the femoral component is tapered on both the anterior-posterior sides and the medial-lateral sides i.e. when it has a double taper. Polymer portions of different thicknesses may be used, as described before.

Figure 5:
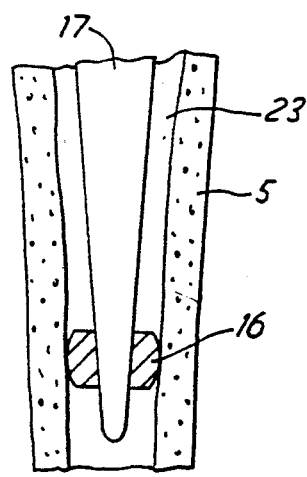
FIG. 5 is a diagram of the lower part of the femoral stem in the medullary canal of a femur showing the optional tip spacer in position.
Figure 6:
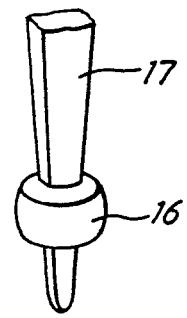
FIG. 6 is a sketch of the optional tip spacer mounted on the lower part of the femoral stem.

The stability of the femoral component inside the femoral medullary canal can be further improved with the use of a spacer 16 shown in FIGS. 5 and 6. the spacer is a push fit onto the distal tip 17 of the femoral stem 1 and is an approximate fit in the distal femoral medullary canal 23. The spacer/stabiliser is an optional feature of the invention and may be used or not according to the desires of the surgeon. The device may be made from any suitable biocompatible material such as medical grade silicone rubber or high density polyethylene. The spacer/stabilizer is not intended to be a close fit in the medullary canal like the already well known bone cement plugs, but acts in a similar way to those devices described by the inventors in our British Patent No. 1409053. It allows the stem to move down the medullary canal.

While the invention has been illustrated by reference to preferred embodiments it will be understood by those skilled in the art that various changes may be made without departing from the spirit and scope of the invention, and it is intended to cover all such changes by the appended claims.

We claim:

1. A cementless method of securing a bone implant assembly in a bone cavity bounded by a cavity wall, comprising the steps of: providing an assembly comprising a bone implant element having a tapered elongate stem for insertion into a bone cavity, and at least two wedge means adapted to engage fixedly with respective surfaces thereof the wall of the cavity and simultaneously to engage slidably with respective surfaces thereof the stem; locating the wedge means on opposed surface portions of the stem; and pushing the wedge means and stem at least partially into the cavity so that the wedge means are urged radially outwardly and mutually apart so as to wedge between proximal regions of the cavity wall and the stem; and subsequently allowing the stem to move more deeply into the cavity with relative sliding between the stem and the wedge means so that the latter are thereby urged outwardly to transmit forces to the cavity wall.

2. A bone implant assembly comprising a bone implant element having a tapered elongate stem for insertion into a bone cavity which is delimited by a bone cavity wall and having a proximal mouth through which the stem is inserted; the bone implant assembly further comprising a wedge assembly comprising at least two wedge means for slidably engaging respective opposed surface portions of a proximal portion of the stem so as to be slidable therealong and for, when the stem is located in said bone cavity, simultaneously fixedly engaging respective opposed portions of a proximal region of the bone cavity wall such that the stem is insertable further into the cavity with concomitant sliding of the stem relative to the wedge means so that the latter are thereby urged radially outwardly and mutually apart and thereby transmit forces to said opposed portions of the proximal region of the bone cavity wall.

15. A bone implant assembly according to claim 9 wheein said wedge means are formed from a plurality of inner portions of different dimensions selectively attachable to an outer portion so as to produce wedge means of different dimensions.

3. Bone implant assembly according to claim 2 wherein each said wedge means has a portion of low-friction, low-wear material which provides the stem engaging surface.

4. Bone implant assembly according to claim 2 wherein the wedge means includes a wall engaging surface which is adapted for non-slipping contact with the wall.

5. Bone implant assembly according to claim 2 wherein the stem has lateral and medial sides and the wedge assembly comprises two wedge means for engaging the lateral and medial sides of the stem respectively.

6. Bone implant assembly according to claim 5 wherein the medial wedge means for engaging the medial side of the stem has lip means for engaging the bone around the mouth of the cavity to prevent the medial wedge means from moving distally down the cavity.

7. Bone implant assembly according to claim 5 wherein the wedge assembly includes separate anterior and posterior wedge means.

8. Bone implant assembly according to claim 2 wherein at least one wedge means comprises an inner portion of a low friction material which provides the stem engaging surface; and an outer portion of implant grade metal of the same composition as the stem.

9. A bone implant assembly according to claim 8 wherein said inner portion and outer portion are mutually detachable.

10. Bone implant assembly according to claim 2 wherein at least one said wedge means is elongate and has transverse slots enabling deformation of said at least one wedge means.

* * * * *